United States Patent [19]

Chang et al.

[11] Patent Number: 5,516,954
[45] Date of Patent: * May 14, 1996

[54] PROCESS FOR PREPARING LONG CHAIN ALKYLAROMATIC COMPOUNDS

[75] Inventors: Clarence D. Chang, Princeton; Scott Han, Lawrenceville, both of N.J.; José G. Santiesteban, Yardley, Pa.; Margaret M. Wu, Skillman, N.J.; Yusheng Xiong, Newtown, Pa.

[73] Assignee: Mobil Oil Corporation, Fairfax, Va.

[ * ] Notice: The portion of the term of this patent subsequent to Dec. 28, 2014, has been disclaimed.

[21] Appl. No.: 344,327

[22] Filed: Nov. 23, 1994

Related U.S. Application Data

[63] Continuation of Ser. No. 121,629, Sep. 16, 1993, abandoned.
[51] Int. Cl.⁶ .................................................... C07C 2/64
[52] U.S. Cl. ............................................ 585/467; 585/446
[58] Field of Search ...................................... 585/467, 475

[56] References Cited

U.S. PATENT DOCUMENTS

| | | | |
|---|---|---|---|
| 3,153,677 | 10/1964 | Domash et al. | 585/467 |
| 3,692,696 | 9/1972 | Kravitz et al. | 252/439 |
| 4,259,537 | 3/1981 | Chu | 585/467 |
| 5,396,011 | 3/1995 | Kuhn | 585/455 |

FOREIGN PATENT DOCUMENTS 1-288339  11/1989  Japan .

OTHER PUBLICATIONS

European Publication No. WO 94/14732 (Jul. 7, 1994).

*Primary Examiner*—Ponnathapura Achutamurthy
*Attorney, Agent, or Firm*—Ronald A. Bleeker; Dennis P. Santini; Lori F. Cuomo

[57] ABSTRACT

Long chain alkyl aromatic compounds are prepared by alkylating an alkylatable aromatic compound with a long chain alkylating agent in the presence of a catalyst comprising an acidic solid material which comprises a Group IVB metal oxide, such as zirconia, modified with an oxyanion of a Group VIB metal, such as tungstate.

20 Claims, No Drawings

PROCESS FOR PREPARING LONG CHAIN ALKYLAROMATIC COMPOUNDS

RELATED APPLICATION

This application is a continuation of application Ser. No. 08/121,629 filed Sep. 16, 1993, entitled Process for Preparing Long Chain Alkylaromatic Compounds, now abandoned, incorporated herein in its entirety by reference.

BACKGROUND

The present invention relates to a process for preparing long chain alkyl aromatic compounds by alkylating an aromatic compound with a relatively long chain alkylating agent employing a particular acidic solid material as a catalyst. This acidic solid comprises a Group IVB metal oxide, such as zirconia, modified with an oxyanion of a Group VIB metal, such as tungstate.

The alkylation of aromatic hydrocarbons with an olefin in the presence of a zeolite having uniform pore openings of from about 6 to about 15 Angstrom units is described in U.S. Pat. No. 2,904,607. U.S. Pat. No. 3,251,897 describes the alkylation of aromatic hydrocarbons in the presence of X- or Y-type zeolites, specifically such type zeolites wherein the cation is a rare earth metal species and/or hydrogen. U.S. Pat. Nos. 3,751,504 and 3,751,506 describe the vapor phase alkylation of aromatic hydrocarbons with olefins, e.g., benzene with ethylene, in the presence of a catalyst comprising, for example, ZSM-5.

U.S. Pat. Nos. 3,631,120 and 3,641,177, describe a liquid phase process for the alkylation of aromatic hydrocarbons with olefins in the presence of certain zeolites.

U.S. Pat. Nos. 4,301,316 and 4,301,317 disclose the use of such zeolites as ZSM-4, ZSM-20, ZSM-38, mazzite, Linde Type L and zeolite Beta to catalyze the alkylation of benzene with relatively long chain olefins to produce long chain alkylbenzenes.

U.S. Pat. No. 4,962,256 describes an alkylation process utilizing, as a catalyst, a zeolite designated as MCM-22. In this process, aromatics are alkylated with long-chain olefins.

SUMMARY

There is provided a process for preparing long chain alkyl aromatic compounds which comprises contacting at least one alkylatable aromatic compound with at least one alkylating agent possessing an alkylating aliphatic group having at least six carbon atoms under alkylation reaction conditions and in the presence of an alkylation catalyst to provide an alkylated aromatic product possessing at least one alkyl group derived from said alkylating agent, said catalyst comprising an acidic solid comprising a Group IVB metal oxide, such as zirconia, modified with an oxyanion of a Group VIB metal.

There is also provided a process for alkylating an alkylatable polynuclear aromatic hydrocarbon which comprises contacting the alkylatable polynuclear aromatic hydrocarbon with an olefinic alkylating agent having at least about 6 carbon atoms under alkylation reaction conditions and in the presence of an alkylation catalyst comprising an acidic solid comprising a Group IVB metal oxide, such as zirconia, modified with an oxyanion of a Group VIB metal.

EMBODIMENTS

The term "aromatic" in reference to the alkylatable compounds which are useful herein is to be understood in accordance with its art-recognized scope which includes alkyl substituted and unsubstituted mono- and polynuclear compounds. Compounds of an aromatic character which possess a hetero atom are also useful provided they do not act as catalyst poisions under the reaction conditions selected.

Substituted aromatic compounds which can be alkylated herein must possess at least one hydrogen atom directly bonded to the aromatic nucleus. The aromatic rings can be substituted with one or more alkyl, aryl, alkaryl, alkoxy, aryloxy, cycloalkyl, halide, and/or other groups which do not interfere with the alkylation reaction.

Suitable aromatic hydrocarbons include benzene, toluene, xylene, naphthalene, anthracene, naphthacene, perylene, coronene, phenanthrene, and alkyl-substituted derivatives of these aromatic hydrocarbons. Generally the alkyl groups which can be present as substituents on the aromatic compound contain from one to about 22 carbon atoms and preferably from about one to eight carbon atoms, and most preferably from about one to four carbon atoms.

Suitable alkyl substituted aromatic compounds include toluene, xylene, isopropylbenzene, normal propylbenzene, alpha-methylnaphthalene, ethylbenzene, cumene, mesitylene, durene, p-cymene, butylbenzene, pseudocumene, o-diethylbenzene, m-diethylbenzene, p-diethylbenzene, isoamylbenzene, isohexylbenzene, pentaethylbenzene, pentamethylbenzene; 1,2,3,4- tetraethylbenzene; 1,2,3,5-tetramethylbenzene; 1,2,4-triethylbenzene; 1,2,3-trimethylbenzene, m-butyltoluene; p-butyltoluene; 3,5-diethyltoluene; o-ethyltoluene; p-ethyltoluene; m-propyltoluene; 4-ethyl-m-xylene; dimethylnaphthalenes; ethylnaphthalene; 2,3-dimethylanthracene; 9-ethylanthracene; 2-methylanthracene; o-methylanthracene; 9,10-dimethylphenanthrene; and 3-methyl-phenanthrene. Higher molecular weight alkylaromatic hydrocarbons can also be used as starting materials and include aromatic hydrocarbons such as are produced by the alkylation of aromatic hydrocarbons with olefin oligomers. Such product are frequently referred to in the art as alkylate and include hexylbenzene, nonylbenzene, dedecylbenzene, pentadecylbenzene, hexyltoluene, nonyltoluene, dodecyltoluene, pentadecytoluene, etc. Very often alkylate is obtained as a high boiling fraction In which the alkyl group attached to the aromatic nucleus varies in size from about $C_6$ to about $C_2O$.

Reformate containing substantial quantities of benzene, toluene and/or xylene constitutes a particularly useful feed for the alkylation process of this invention.

The alkylating agents which are useful in the process of this invention generally include any aliphatic or aromatic organic compound having one or more available alkylating aliphatic groups capable of reaction with the alkylatable aromatic compound. The alkylatable group itself should have at least about 6 carbon atoms, preferably at least about 8, and still more preferably at least about 12 carbon atoms. Examples of suitable alkylating agents are olefins such as hexenes, heptenes, octenes, nonenes, decenes, undecenes, dodecenes, and the like: alcohols (inclusive of monoalcohols, dialcohols, trialcohols, etc.) such as hexanols, heptanols, octanols, nonanole, decanols, undecanols and dodecanols; and alkyl halides such as hexyl chlorides, octyl chlorides, dodecyl chlorides; and, higher homologs of the foregoing. Branched alkylating agents, especially oligomerized olefins such as the trimers, tetramers, pentamers, etc., of light olefins such as ethylene, propylene, the butylenes, etc., are also useful herein. Olefin oligomers described in U.S. Pat. No. 5,026,933 may be used as alkylating agents in the present process.

The alkylaromatic products produced by the present process are useful as synthetic lubricants. More particularly, alkylaromatic fluids have been proposed for use as certain types of functional fluids where good thermal and oxidative stability are required. For example, U.S. Pat. No. 4,714,794 (Yoshida) describes the monoalkylated naphthalenes as having excellent thermal and oxidative stability, low vapor pressure and flash point, good fluidity and high heat transfer capacity and other properties which render them suitable for use as thermal medium oils. The use of a mixture of monoalkylated and polyalkylated naphthalenes as a base for synthetic functional fluids is described in U.S. Pat. No. 4,604,491 (Dressier) and Pellegrini U.S. Pat. Nos. 4,211,655 and 4,238,343 describe the use of alkylaromatics as transformer oils. Properties of alkylated naphthalene lubricants are further discussed in U.S. Pat. No. 5,034,563.

Alkylated benzenes prepared by the present process are useful as synthetic lubricants and as intermediates for the preparation of detergents. More particularly, the alkylbenzenes prepared by the above-discussed alkylation process are useful as intermediates for the production of alkylphenylsulfonates, which are useful as detergents or surfactants. Processes for sulfonating alkylbenzenes are described in U.S. Pat. No. 4,298,547. More particularly, alkylbenzenes may be converted to alkylphenylsulfonates by sulfonation of the aromatic ring with sulfuric acid. The reaction is well known in the art and is commonly carried out by contacting the organic compound with sulfuric acid at temperatures of from about −70° C. to about +60° C. Detailed descriptions of specific commercial processes abound in the literature. See, for instance, W. L. Faith et al., *Industrial Chemicals*, 3rd ed., 60–62 (1966). Those skilled in the field need only refer to the conventional literature for instruction on how to carry out such reactions.

The catalyst described herein comprises an oxide of a Group IVB metal, preferably zirconia or titania. This Group IVB metal oxide is modified with an oxyanion of a Group VIB metal, such as an oxyanion of tungsten, such as tungstate. The modification of the Group IVB metal oxide with the oxyanion of the Group VIB metal imparts acid functionality to the material. The modification of a Group IVB metal oxide, particularly, zirconia, with a Group VIB metal oxyanion, particularly tungstate, is described in U.S. Pat. No. 5,113,034; in Japanese Kokai Patent Application No. Hei 1 [1989]-288339; and in an article by K. Arata and M. Hino in *Proceedings 9th International Congress on Catalysis*, Volume 4, pages 1727–1735 (1988), the entire disclosures of these publications are expressly incorporated herein by reference.

According to an optional modification of the Group IVB metal oxide described herein, a hydrogenation/dehydrogenation component is combined with the Group IV metal oxide. This hydrogenation/dehydrogenation component imparts the ability of the material to catalyze the addition of hydrogen to or the removal of hydrogen from organic compounds, such as hydrocarbons, optionally substituted with one or more heteroatoms, such as oxygen, nitrogen, metals or sulfur, when the organic compounds are contacted with the modified material under sufficient hydrogenation or dehydrogenation conditions.

Examples of hydrogenation/dehydrogenation components include the oxide, hydroxide or free metal (i.e., zero valent) forms of Group VIII metals (i.e., Pt, Pd, Ir, Rh, Os, Ru, Ni, Co and Fe), Group IVA metals (i.e., Sn and Pb), Group VB metals (i.e., Sb and Bi) and Group VIIB metals (i.e., Mn, Tc and Re). The present catalyst may comprise one or more catalytic forms of one or more noble metals (i.e., Pt, Pd, Ir, Rh, Os or Ru). Combinations of catalytic forms of such noble or non-noble metals, such combinations of Pt with Sn, may be used. The valence state of the metal of the hydrogenation/dehydrogenation component is preferably in a reduced valance state, e.g., when this component is in the form of an oxide or hydroxide. The reduced valence state of this metal may be attained, in situ, during the course of a reaction, when a reducing agent, such as hydrogen, is included in the feed to the reaction.

For the purposes of the present disclosure, the expression, Group IVB metal oxide modified with an oxyanion of a Group VIB metal, is intended to connote a material comprising, by elemental analysis, a Group IVB metal, a Group VIB metal and oxygen, with more acidity than a simple mixture of separately formed Group IVB metal oxide mixed with a separately formed Group VIB metal oxide or oxyanion. The present Group IVB metal, e.g., zirconium, oxide modified with an oxyanion of a Group VIB metal, e.g., tungsten, is believed to result from an actual chemical interaction between a source of a Group IVB metal oxide and a source of a Group VIB metal oxide or oxyanion.

This chemical interaction is discussed in the aforementioned article by K. Arata and M. Hino in *Proceedings 9th International Congress on Catalysis*, Volume 4, pages 1727– 1735 (1988). In this article, it is suggested that solid superacids are formed when sulfates are reacted with hydroxides or oxides of certain metals, e.g., Zr. These superacids are said to have the structure of a bidentate sulfate ion coordinated to the metal, e.g., Zr. In this article, it is further suggested that a superacid can also be formed when tungstates are reacted with hydroxides or oxides of Zr. The resulting tungstate modified zirconia materials are theorized to have an analogous structure to the aforementioned superacids comprising sulfate and zirconium, wherein tungsten atoms replace sulfur atoms in the bidentate structure.

Although it is believed that the present catalysts may comprise the bidentate structure suggested in the aforementioned article by Arata and Hino, the particular structure of the catalytically active site in the present Group IVB metal oxide modified with an oxyanion of a Group VIB metal has not yet been confirmed, and it is not intended that this catalyst component should be limited to any particular structure.

Other elements, such as alkali (Group IA) or alkaline earth (Group IIA) compounds may optionally be added to the present catalyst to alter catalytic properties. The addition of such alkali or alkaline earth compounds to the present catalyst may enhance the catalytic properties of components thereof, e.g., Pt or W, in terms of their ability to function as a hydrogenation/dehydrogenation component or an acid component.

The Group IVB metal (i.e., Ti, Zr or Hf) and the Group VIB metal (i.e., Cr, Mo or W) species of the present catalyst are not limited to any particular valence state for these species. These species may be present in this catalyst in any possible positive oxidation value for these species. Subjecting the catalyst, e.g., when the catalyst comprises tungsten, to reducing conditions, e.g., believed to be sufficient to reduce the valence state of the tungsten, may enhance the overall catalytic ability of the catalyst to catalyze certain reactions, e.g., the isomerization of n-hexane.

Suitable sources of the Group IVB metal oxide, used for preparing the present catalyst, include compounds capable of generating such oxides, such as oxychlorides, chlorides, nitrates, etc., particularly of zirconium or titanium. Alkoxides of such metals may also be used as precursors or sources of the Group IVB metal oxide. Examples of such alkoxides include zirconium n-propoxide and titanium i-propoxide. Preferred sources of a Group IVB metal oxide are zirconium hydroxide, i.e., $Zr(OH)_4$, and hydrated zirconia. The expression, hydrated zirconia, is intended to connote materials comprising zirconium atoms covalently linked to other zirconium atoms via bridging oxygen atoms, i.e., Zr-O-Zr, further comprising available surface hydroxy groups. These available surface hydroxyl groups are believed to react with the source of an anion of a Group IVB metal, such as tungsten, to form the present acidic catalyst component. As suggested in the aforementioned article by K. Arata and M. Hino in *Proceedings 9th International Congress on Catalysis,* Volume 4, pages 1727–1735 (1988), precalcination of $Zr(OH)_4$ at a temperature of from about 100° C. to about 400° C. results in a species which interacts more favorably with tungstate. This precalcination is believed to result in the condensation of ZrOH groups to form a polymeric zirconia species with surface hydroxyl groups. This polymeric species is referred to herein as a form of a hydrated zirconia.

Treatment of hydrated zirconia with a base solution prior to contact with a source of tungstate may be preferable. More particularly, refluxing hydrated zirconia in an $NH_4OH$ solution having a pH of greater than 7, e.g., about 9, was beneficial. Without wishing to be bound by any theory, it is theorized that the base-treated, hydrated zirconia is better because it has higher surface area. It is also theoretically possible that the base treatment alters surface hydroxyl groups on the hydrated zirconia, possibly in a manner which promotes a more desirable interaction with the source of tungstate later used.

Suitable sources for the oxyanion of the Group VIB metal, preferably molybdenum or tungsten, include, but are not limited to, ammonium metatungstate or metamolybdate, tungsten or molybdenum chloride, tungsten or molybdenum carbonyl, tungstic or molybdic acid and sodium tungstate or molybdate.

The present catalyst may be prepared, for example, by impregnating the hydroxide or oxide, particularly the hydrated oxide, of the Group IVB metal with an aqueous solution containing an anion of the Group VIB metal, preferably tungstate or molybdate, followed by drying. Calcination of the resulting material may be carried out, preferably in an oxidizing atmosphere, at temperatures from about 500° C. to about 900° C., preferably from about 700° C. to about 850° C., and more preferably from about 750° C. to about 825° C. The calcination time may be up to 48 hours, preferably for about 0.5–24 hours, and more preferably for about 1.0–10 hours. In a most preferred embodiment, calcination is carried out at about 800° C. for about 1 to about 3 hours.

When a source of the hydroxide or hydrated oxide of zirconium is used, calcination, e.g., at temperatures greater than 500° C., of the combination of this material with a source of an oxyanion of tungsten may be needed to induce the theorized chemical reaction which imparts the desired degree of acidity to the overall material. However, when more reactive sources of zirconia are used, it is possible that such high calcination temperature may not be needed.

In the present catalyst, of the Group IVB oxides, zirconium oxide is preferred; and of the Group VIB anions, tungstate is preferred.

Qualitatively speaking, elemental analysis of the present catalyst will reveal the presence of Group IVB metal, Group VIB metal and oxygen. The amount of oxygen measured in such an analysis will depend on a number of factors, such as the valence state of the Group IVB and Group VIB metals, the form of the hydrogenation/dehydrogenation component, moisture content, etc. Accordingly, in characterizing the composition of the present catalyst, it is best not to be restricted by any particular quantities of oxygen. In functional terms, the amount of Group VIB oxyanion in the present catalyst may be expressed as that amount which increases the acidity of the Group IVB oxide. This amount is referred to herein as an acidity increasing amount. Elemental analysis of the present catalyst may be used to determine the relative amounts of Group IVB metal and Group VIB metal in the catalyst. From these amounts, mole ratios in the form of $XO_2/YO_3$ may be calculated, where X is said Group IVB metal, assumed to be in the form $XO_2$, and Y is said Group VIB metal, assumed to be in the form of $YO_3$. It will be appreciated, however, that these forms of oxides, i.e., $XO_2$ and $YO_3$, may not actually exist, and are referred to herein simply for the purposes of calculating relative quantities of X and Y in the present catalyst. The present catalysts may have calculated mole ratios, expressed in the form of $XO_2/YO_3$, where X is at least one Group IVB metal (i.e., Ti, Zr, and Hf) and Y is at least one Group VIB metal (i.e., Cr, Mo, or W), of up to 1000, e.g., up to 300, e.g., from 2 to 100, e.g., from 4 to 30.

The acidic solid material prepared as above for use herein can be shaped into a wide variety of particle sizes. Generally speaking, the particles can be in the form of a powder, a granule, or a molded product, such as an extrudate having particle size sufficient to pass through a 2 mesh (Tyler) screen and be retained on a 400 mesh (Tyler) screen. In cases where the catalyst is molded, such as by extrusion, the acidic solid can be extruded before drying or partially dried and then extruded.

As mentioned previously, the catalyst described herein can optionally be used in intimate combination with a hydrogenating component such as tungsten, vanadium, molybdenum, rhenium, nickel, cobalt, chromium, manganese, or a noble metal such as platinum or palladium. Such component can be introduced in the catalyst composition by way of co-precipitation, exchanged into the composition, impregnated therein, or intimately physically admixed therewith. Such component can be impregnated in, or on, the acidic solid material such as, for example, by, in the case of platinum, treating the acidic solid material with a solution containing a platinum metal-containing ion. Thus, suitable platinum compounds for this purpose include chloroplatinic acid, platinum halides, and various compounds containing the platinum ammine complex.

Prior to its use in a catalytic process, the acidic solid material may be dehydrated, at least partially. This can be done by heating the solid material to a temperature in the range of from about 200° C. to about 595° C. in an atmosphere such as air, nitrogen, etc., and at atmospheric, subatmospheric or superatmospheric pressures for between about 30 minutes to about 48 hours. Dehydration can also be performed at room temperature merely by placing the material in a vacuum, but a longer time is required to obtain a sufficient amount of dehydration.

It may be desired to incorporate the acidic solid material with another material resistant to the temperatures and other conditions employed in organic conversion processes. Such other materials include active and inactive materials and synthetic or naturally occurring zeolites as well as inorganic materials such as clays, silica and/or metal oxides such as alumina. The latter may be either naturally occurring or in the form of gelatinous precipitates or gels including mixtures of silica and metal oxides. Use of another material in conjunction with the acidic solid material, i.e., combined therewith or present during synthesis of the acidic solid material, which is active, tends to change the conversion and/or selectivity of the catalyst in certain organic conversion processes. Inactive materials suitably serve as diluents to control the amount of conversion in a given process so that products can be obtained economically and orderly without employing other means for controlling the rate of reaction. The acidic solid materials may be incorporated into naturally occurring clays, e.g., bentonite and kaolin, to improve the crush strength of the catalyst under commercial operating conditions. These other materials, i.e., clays, oxides, etc., function as binders for the catalyst. It is desirable to provide a catalyst having good crush strength because in commercial use it is desirable to prevent the catalyst from breaking down into powder-like materials. These clay and/or oxide binders have been employed normally only for the purpose of improving the crush strength of the catalyst.

Naturally occurring clays which can be composited with the acidic solid material include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification. Binders useful for compositing with the present acidic solid material also include inorganic oxides, notably alumina.

In addition to the foregoing materials, the acidic solid material can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia silica-alumina-magnesia and silica-magnesia-zirconia.

The relative proportions of finely divided acidic solid material and inorganic oxide matrix vary widely, with the crystal content ranging from about 1 to about 90 percent by weight and more usually, particularly when the composite is prepared in the form of beads, in the range of about 2 to about 80 weight percent of the composite.

The alkylation process of this invention is conducted such that the organic reactants, i.e., the alkylatable aromatic compound and the alkylating agent, are brought into contact with the catalyst composition in a suitable reaction zone such as, for example, in a flow reactor containing a fixed bed of the catalyst composition, under effective alkylation conditions. Such conditions include a temperature of from about 0° C. to about 500° C., a pressure of from about 0.2 to about 250 atmospheres, a feed weight hourly space velocity (WHSV) of from about 0.1 $hr^{-1}$ to about 500 $hr^{-1}$ and an alkylatable aromatic compound to alkylating agent mole ratio of from about 0.1:1 to about 50:1. The WHSV is based upon the weight of the catalyst composition employed, i.e., the total weight of active catalyst (and binder if present). Preferred reaction conditions include a temperature within the approximate range of from about 25° C. to about 350° C., a pressure of from about 1 to about 25 atmospheres, a WHSV of from about 0.5 $hr^{-1}$ to about 100 $hr^{-1}$ and an alkylatable aromatic compound to alkylating agent mole ratio of from about 0.5:1 to about 5:1. The reactants can be in either the vapor phase or the liquid phase and can be neat, i.e., free from intentional admixture or dilution with other material, or they can be brought into contact with the catalyst composition with the aid of carrier gases or diluents such as, for example, hydrogen or nitrogen.

The alkylation process described herein can be carried out as a batch-type, semi-continuous or continuous operation utilizing a fixed or moving bed catalyst system. A preferred embodiment entails use of a catalyst zone wherein the hydrocarbon charge is passed concurrently or countercurrently through a moving bed of particle-form catalyst. The latter, after use, is conducted to a regeneration zone where coke is burned from the catalyst in an oxygen-containing atmosphere (such as air) at elevated temperature, after which the regenerated catalyst is recycled to the conversion zone for further contact with the organic reactants.

The present alkylation process may be carried out by contacting an olefin and aromatic compound with the catalyst at 25°–200° C., preferably in a range of 50°–120° C. More preferably, the olefin is added slowly to the aromatics in the presence of catalyst to prevent homopolymerization of olefin.

The observed product alkylaromatics have unique isomer distribution which translate into improved properties in numerous applications. For example, the linear alkyl benzene is richer in 2-phenylalkane isomer which is a precursor for biodegradable detergents. The alkylnaphthalenes (AN) which have been produced over the present catalyst have very high alpha/beta ratio, a property associated with high thermal/oxidative stability, and very high 2-naphthylalkane isomer content, a property that leads to high viscosity index. As a result, the AN produced by this catalyst is an excellent synthetic lubricant base stock.

For benzene alkylation with alpha olefins, the present process produced a product wherein 2-phenylalkane is the major component with less amounts of 3-, 4-, 5-phenylalkanes. The alkylbenzenes from such catalytic reactions are highly linear, at least >98%. Linear alkylbenzenes (LABs) with high 2-phenyl content have higher biodegradability.

For alkylnaphthalenes, in addition to high 2-naphthylalkane content, the present products also contain more 1-alkylnaphthalene (the $\alpha$ isomer) relative to the 2-alkylnaphthalene (the $\beta$ isomer).

The naphthylalkane product of the present process, particularly the monoalkylated product, may have a mole ratio of the $\alpha$ isomer to the $\beta$ isomer (i.e., an $\alpha/\beta$ ratio) of greater than 2, and this product may also have a 2-naphthylalkane content of greater than 50%, based upon the total moles of monoalkylated product. This product may also contain a minor amount, e.g., from 5 to 25 wt. %, of polyalkylated product, such as dialkylated and trialkylated product. This product may be used as a lubricant formulation by itself or blended with other synthetic or mineral stocks and/or typical lubricant additives. U.S. Pat. Nos. 4,714,794 and 5,177,284 discuss uses of various alkylated naphthalenes.

The spent catalyst can be regenerated by air calcination at 500° C. for 1 hour, followed by reduction in hydrogen at 350° C. for 15 hours.

EXAMPLE 1

One part by weight of zirconyl chloride, $ZrOCl_2 \cdot 8H_2O$, was dissolved in 10 parts $H_2O$ and concentrated $NH_4OH_{(aq)}$ added until the solution pH was ~9. The resulting slurry, $Zr(OH)_4$, was filtered and washed with 10 parts of distilled, deionized water.

One part by weight of this filtered wet cake was mixed with 10 parts of distilled, deionized water and the pH of the mixture set to pH ~9 with concentrated $NH_4OH$. This mixture was refluxed for 16 hours, cooled, filtered, and washed with 10 parts of water. The solid was air dried at 130° C. for 16 hours.

Approximately 3.7 parts by weight of the resulting $Zr(OH)_4$ were impregnated via incipient wetness with 1.8 parts of an aqueous solution containing 1 part of ammonium metatungstate, $(NH_4)_6H_4W_{12}O_4O$. The resulting material was dried for 2 hours at 120° C. and then calcined at 825° C. in flowing air for 3 hours. The sample was calcined at 350° C. for 15 hours under flowing hydrogen prior to catalytic testing. This sample had a calculated mole ratio of $ZrO_2/WO_2$ of 5.7.

EXAMPLE 2

This Example illustrates the alkylation of benzene with 1-decene. 33.7 g (0.24 mole) of 1-decene was added slowly to a suspension of the catalyst from Example 1 (2 g) in 49.6 g (excess) of benzene heated to 75° C. After the addition was completed (in about 1.5 hour), the reaction mixture was stirred at 75° C. for another hour. The catalyst was removed by filtration and excess benzene and unreacted 1-decene ($C_{10}=$) was removed by rotary evaporation. The crude product was fractionated to give 25.5 g of decylbenzene (49% yield), 1.0 g of decene dimer (1.4%) and 7.0 g of didecylbenzene (16%). The decylbenzene isomer distribution was 2-phenyldecane, 50.7%; 3-phenylbenzene, 21.7%; 4-phenylbenzene, 14.5%; and 4-phenylbenzene, 13.0%.

EXAMPLE 3

A solution of naphthalene (16.3 g, 0.127 mole) in 25 ml of heptane was heated to 80° C. in the presence of 3 g of the catalyst. 1-decene, 14.9 g (0.106 mole), was added quickly. The reaction was stirred at 80° C. for 8 hours. The catalyst was removed by filtration and the excess naphthalene removed by rotary evaporation. The product was fractionated to give 11.5 g (40% yield) of decylnaphthalene, and 12.4 g (57.3% yield) of didecylnaphthalene. The didecylnaphthalene has KV: 9.9 cS @ 100° C.; 97 cS @ 40° C.; VI 87.

EXAMPLES 4 AND 5

Naphthalene was alkylated with 1-decene under the same conditions as Example 3 with varying amounts of reactants. Table 1 summarizes the amount of reactants and results for Examples 3–5.

TABLE 1

| | Alkylation of Naphthalene with 1-decene | | | | | |
|---|---|---|---|---|---|---|
| Example | NAPH | $C_{10} =$ | Catalyst | Conversion | Monoalkyl | Dialkyl |
| 3 | 16.3 g | 14.9 g | 3 g (10%) | 97% | 41% | 57% |
| 4 | 51 g | 19.5 g | 2 g (5%) | 97% | 81% | 16% |
| 5 | 31.2 g | 71.6 g | 1.1 g (1%) | 64% | (mixture of mono-, di-, tri-alkylated) | |

EXAMPLES 6–10

These Examples demonstrate the alkylation of naphthalene with 1-tetradecene. The reactions were carried out in the same conditions as described in Example 3. The results are tabulated in Table 2.

TABLE 2

Alkylation of Naphthalene with 1-tetradecene

| Example | 6 | 7 | 8 | 9 | 10 |
|---|---|---|---|---|---|
| Olefin, $C_{14}=$ | 51.1 g | 22.1 g | 22.1 g | 22.1 g | 387 g |
| Naphthalene | 16 g | 6.5 g | 6.5 g | 6.6 g | 120 g |
| O/N ratio | 2.1 | 2.2 | 2.2 | 2.2 | 2.1 |
| Catalyst | 2.0 g | 1.0 g | 1.0 g | 1.0 g | 10 g |
| wt. % | 3 | 3.5 | 3.5 | 3.5 | 2 |
| Temperature | 75° C. | 50° C. | 80° C. | 100° C. | 80° C. |
| Time | 2 hr. | 3.5 hr. | 2 hr. | 2 hr. | 7 hr. |
| Yield | 89% | 77% | 79% | 77% | 72% |
| GC Analysis* | | | | | |
| Mono-alkylated | 37% | 26.5% | 26.3% | 26.7% | 33% |
| Di-alkylated | 50% | 47.5% | 47.4% | 49.9% | 50.8% |
| Tri-alkylated | 13% | 26.0% | 26.3% | 23.4% | 16.2% |
| α/β Ratio# | 2.7 | 3.5 | 2.8 | 2.1 | 2.5 |
| Viscosity | | | | | |
| @100° C., cS | 8.12 | 8.62 | 9.40 | 8.90 | 7.87 |
| @40° C., cS | 57.72 | 57.11 | 70.27 | 62.10 | 55.61 |
| VI | 108.6 | 125.2 | 111.3 | 118.5 | 107.0 |
| Pour Point | −35° C. | −33° C. | −32° C. | −35° C. | −35° C. |

*In a higher resolution GC, the mono-fraction ($C_{24}$) contains about 5% of dimers of olefin.
This ratio was measured: in 1H-NMR "benzylic" protons.

The tetradecylnaphthalene isomer distributions were analyzed by GC-MASS. The results for Example 6 are β-2-naphthyltetradecane (18.1%), α-2-(42.5%), β-3-(7.7&), α-3( 11.1%), β-4-(0.3%), β-5- ( 2.4 % ), α-4, β-6, β-7 (10.9%), α-5-( 4.3%), α-6-(1.7%), α-7-(1.0%). Total α/β ratio is 2.4 for the monoalkylnaphthalenes and 2.7 for the mixture.

EXAMPLES 11–15

These Examples demonstrate the alkylation of naphthalene using hexadecene. Conditions and results are summarized in Table 3.

TABLE 3

Alkylation of Naphthalene with 1-hexadecene

| Example | 11 | 12 | 13 | 14 | 15 |
|---|---|---|---|---|---|
| Olefin, $C_{16}=$ | 31.3 g | 250 g | 250 g | 392 g | 392 g |
| Naphthalene | 30 g | 130 g | 200 g | 450 g | 450 g |
| O/N ratio | 0.61 | 1.1 | 1 | 0.5 | 0.5 |
| Catalyst | 3.25 g | 11.5 g | 10.4 g | 22.6 g# | 31 g |
| wt. % | 5.3 | 3.0 | 2.3 | 2.7 | 3.7 |
| Temperature | 80° C. | 80–110° C. | 70° C. | 70° C. | 70° C. |
| Time | 2 hr. | 3.5 hr. | 2 hr. | 2 hr. | 7 hr. |
| $C_{16}=$ conversion | 99% | 99% | 99% | 99% | 99% |
| GC Analysis | | | | | |
| Mono-alkylated | 64.1% | 46.0% | 65.3% | 74.5% | 72.3% |
| Di-alkylated | 34.0% | 39.8% | 29.4% | 20.6% | 25.7% |
| Tri-alkylated | 1.9% | 11.8% | 3.1% | 1.7% | 2.0% |
| Olefin Dimer | 0% | 2.4% | 2.2% | 3.2% | — |
| α/β Ratio | 2.6 | 1.7 | 2.8 | 2.6 | 2.3 |
| Viscosity | | | | | |
| @100° C., cS | 6.18 | 8.29 | 6.4 | 5.58 | 5.82 |
| @40° C., cS | 38.87 | 56.92 | 40.03 | 32.59 | 35.63 |
| VI | 105.0 | 116.1 | 109.1 | 108.8 | 104.0 |

Catalyst was regenerated.

Analysis of the isomeric distribution of the monoalkylated AN shows that it is rich in the 2-substituted isomer zeolite catalysts. GC-MASS results for Example 11 are present in Table 4.

TABLE 4

| Isomer Distribution of Mono-alkylated AN in Example 11 | | | | | | | |
|---|---|---|---|---|---|---|---|
| Isomer | 2- | 3- | 4- | 5- | 6- | 7-, 8- | α/β ratio |
| Example 11 | 51.1 | 21.1 | 8.9 | 6.1 | 4.0 | 6.2 | 2.6 |

These data demonstrate that the AN in this Example is rich in the 2-substituted isomer and also has a high alpha/beta substitution ratio.

The catalyst showed very high activity for aromatic alkylation reactions. The reaction can be carried out in lower temperature than normally done with other solid catalysts. Lower reaction temperature is advantageous for increased catalyst life, regenerability, and, more importantly, product selectivity. For example, the LABs are high in 2-phenylalkane content and are, therefore, excellent detergent materials. As lubrication oil components, the alkylnaphthalenes have high $\alpha/\beta$ isomer ratio, resulting in improved thermal and oxidative stability. The higher 2-naphthyalkane isomer content also improves VI of the oil.

What is claimed is:

1. A process for preparing alkylylatable polynuclear aromatic hydrocarbon compounds which comprises contacting at least one alkylatable polynuclear aromatic hydrocarbon compound with at least one alkylating agent possessing an alkylating aliphatic group having at least six carbon atoms under alkylation reaction conditions and in the presence of an alkylation catalyst to provide an alkylated polynuclear aromatic hydrocarbon product possessing at least one alkyl group derived from said alkylating agent, said catalyst comprising an acidic solid comprising a Group IVB metal oxide modified with an oxyanion of a Group VIB metal.

2. A process according to claim 1, wherein said Group IVB metal is zirconium and said Group VIB metal is tungsten.

3. A process according to claim 1, wherein said catalyst comprises a material matrix.

4. A process according to claim 3, wherein said matrix material comprises alumina, silica, or mixture thereof.

5. A process according to claim 3, wherein the catalyst is provided in the form of extrudate, beads, or fluidizable microspheres.

6. A process according to claim 1, wherein the alkylating aliphatic group contains at least about 8 carbon atoms.

7. A process according to claim 1, wherein the alkylating aliphatic group contains at least about 12 carbon atoms.

8. A process according to claim 1, wherein the alkylating agent is an olefin.

9. A process according to claim 1, wherein the alkylating agent is an alcohol.

10. A process according to claim 1, wherein the alkylating agent is an alkyl halide.

11. A process according to claim 1, wherein the alkylatable polynuclear aromatic hydrocarbon compound is selected from the group consisting of naphthalene, anthracene, naphthacone, perylene, coronene and phenanthrene.

12. A process according to claim 1, wherein the alkylation reaction conditions include a temperature of from about 0° C. to about 500° C., a pressure of from about 0.2 to about 250 atmospheres, an WHSV of from about 0.1 $hr^{-1}$ to 500 $hr^{-1}$ and an alkylatable aromatic compound to alkylating agent mole ratio of from about 0.1:1 to 50:1.

13. A process according to claim 1, wherein the alkylation reaction conditions include a temperature of from about 50° C. to 350° C., a pressure of from about 1 to about 25 atmospheres, a WHSV of from about 0.5 $hr^{-1}$ to about 100 $hr^{-1}$ and an alkylatable aromatic compound to alkylating agent mole ratio of from about 0.5:1 to about 5:1.

14. A process for alkylating an alkylatable polynuclear aromatic hydrocarbon which comprises contacting the alkylatable polynuclear aromatic hydrocarbon with an olefinic alkylating agent having at least about 6 carbon atoms under alkylation reaction conditions and in the presence of an alkylation catalyst comprising an acidic solid comprising a Group IVB metal oxide modified with an oxyanion of a Group VIB metal.

15. A process according to claim 14, wherein the polynuclear aromatic hydrocarbon is selected from the group consisting of naphthalene, anthracene, perylene, coronene and phenanthrene.

16. A process according to claim 15, wherein the olefinic alkylating agent contains at least about 12 carbon atoms.

17. A process according to claim 16, wherein the polynuclear aromatic compound is naphthalene.

18. A process according to claim 17, wherein the olefinic alkylating agent is 1-hexadecene.

19. A process for preparing alkylatable polynuclear aromatic hydrocarbon compounds which comprises contacting at least one alkylatable polynuclear aromatic hydrocarbon compound with at least one alkylating agent possessing an alkylating aliphatic group having at least six carbon atoms under alkylation reaction conditions and in the presence of an alkylation catalyst to provide an alkylated polynuclear aromatic hydrocarbon product possessing at least one alkyl group derived from said alkylating agent, said catalyst comprising an acidic solid comprising a Group IVB metal oxide modified with an oxyanion of a Group VIB metal, wherein said contacting is at a temperature in the range of from about 25° to about 200° C.

20. A process for alkylating naphthalene which comprises contacting the naphthalene with an olefinic alkylating agent having at least about 6 carbon atoms under alkylation reaction conditions and in the presence of an alkylation catalyst comprising an acidic solid comprising a Group IVB metal oxide modified with an oxyanion of a Group VIB metal, wherein naphthylalkane product having a mole ratio of 1-alkylnaphthalene to 2-alkylnaphthalene of greater than about 2 is produced.

* * * * *